(12) United States Patent
Livolsi et al.

(10) Patent No.: US 8,147,438 B2
(45) Date of Patent: Apr. 3, 2012

(54) ADJUSTABLE WRIST BRACE

(75) Inventors: Bonnie Livolsi, Monroe Township, NJ (US); Eileen Zirpolo-Kisco, San Marcos, CA (US); Nancy Randall, Roswell, GA (US)

(73) Assignee: DJO, LLC, Vista, CA (US)

( * ) Notice: Subject to any disclaimer, the term of this patent is extended or adjusted under 35 U.S.C. 154(b) by 0 days.

(21) Appl. No.: 12/828,763

(22) Filed: Jul. 1, 2010

(65) Prior Publication Data
US 2011/0130694 A1 Jun. 2, 2011

Related U.S. Application Data (60) Provisional application No. 61/270,109, filed on Jul. 2, 2009.

(51) Int. Cl.
*A61F 5/00* (2006.01)
*A61F 13/00* (2006.01)

(52) U.S. Cl. .................. 602/21; 602/5; 602/20; 602/61; 602/64

(58) Field of Classification Search .......... 602/5, 20–22, 602/60–65; D24/190–192; 128/887, 888, 128/869, 870; 2/16, 17
See application file for complete search history.

(56) References Cited

U.S. PATENT DOCUMENTS

| | | | |
|---|---|---|---|
| 2,206,404 A * | 7/1940 | Jones | 602/21 |
| 4,508,110 A | 4/1985 | Modglin | |
| 4,854,309 A | 8/1989 | Elsey | |
| 5,769,804 A * | 6/1998 | Harris et al. | 602/21 |
| 5,982,285 A | 11/1999 | Bueche et al. | |
| 6,024,715 A | 2/2000 | Maxwell | |
| 6,142,966 A | 11/2000 | Hely | |
| 6,398,748 B1 | 6/2002 | Wilson | |
| 6,540,705 B2 | 4/2003 | Norstrem et al. | |
| 6,893,410 B1 | 5/2005 | Hely | |
| 6,960,176 B1 | 11/2005 | Hely et al. | |
| 7,033,331 B1 | 4/2006 | Hely | |
| 7,056,298 B1 | 6/2006 | Weber | |
| 7,874,997 B2 * | 1/2011 | Jaccard | 602/27 |
| 2006/0069335 A1 * | 3/2006 | Fritsch et al. | 602/5 |
| 2009/0012438 A1 * | 1/2009 | Frangi | 602/21 |

FOREIGN PATENT DOCUMENTS

EP 0842645 6/2003

* cited by examiner

*Primary Examiner* — Kim M Lewis
(74) *Attorney, Agent, or Firm* — Ropes & Gray LLP

(57) ABSTRACT

Provided herein are wrist braces with improved adjustability and performance features. An exemplary wrist brace includes a flexible support casing to enclose a user's wrist; securing loops, mounted substantially along and extending outwardly from the support casing; an elastic securing member passing through at least one of the securing loops; and a puller, attached to the ends of the elastic securing member, configured to adjustably tension the elastic securing member with respect to the casing.

25 Claims, 8 Drawing Sheets

ADJUSTABLE WRIST BRACE

CROSS-REFERENCE TO RELATED APPLICATION

This application claims the benefit of U.S. Provisional Application Ser. No. 61/270,109, filed Jul. 2, 2009, the entire contents of which are incorporated herein by reference.

BACKGROUND

Many individuals suffer from physiological conditions of the upper extremities, including the arm, wrist and hand. For example, carpal tunnel syndrome, which is triggered by pressure on the median nerve, often results in numbness and difficulty with manual tasks and affects many in the general population. Other common conditions include hand and wrist sprains, strains, tendonitis, and nerve compression.

For many affected individuals, the additional support provided to the arm, wrist and hand by a supportive brace may alleviate the pain and degradation of function that may be associated with these physiological conditions. Supportive braces are also often used by athletes and other individuals to improve performance and prevent damage to the joints, muscles, nerves and tissues of the upper extremities.

Existing braces, however, fail to provide support devices that address the needs and desires of users and care providers. For example, Harris et al. (U.S. Pat. No. 5,769,804) describe a carpal tunnel syndrome wrist brace that is secured about a user's wrist by a number of non-elastic laces, threaded through eyelets embedded within a rigid shell and attached to several attachment straps. This brace exhibits a number of disadvantages. First, the use of a rigid shell and non-elastic laces limits the ability of the wrist brace to conform to different user body types and to provide adjustable support for different physiological conditions. Second, the threading of the non-elastic laces through the eyelets is cumbersome because the eyelets are embedded within the shell. Threading laces through embedded eyelets also introduces regions of uneven pressure on the user's skin that may result in irritation and pain.

In another example, Hely (U.S. Pat. No. 6,893,410) describes a brace which is attached to a user's wrist via tightening strands that are anchored in a holder and threaded through openings within the holder. This brace suffers from several of the same disadvantages described above, including impaired adjustability due to the anchored tightening strands, the embedded openings and the uneven pressure caused by the threading of the strands through the openings. Additionally, neither of these braces provides an inner layer that is conformable to a user's skin, nor is dimensioned to provide advantageous supportive forces along a length of a user's arm.

SUMMARY

The apparatus described herein addresses these and other limitations of the prior art by providing wrist braces with improved adjustability and performance features, thereby improving patient compliance. Additionally, use of the wrist braces disclosed herein may decrease the likelihood of complications arising from over-use of a brace. Such risks may include weakness in proximal muscles or the improper formation of scar tissue during healing. The improved ease of consistent and reliable reattachment of the wrist braces described herein may help users overcome the fear of not being able to correctly re-attach the brace after removal, thereby encouraging users to wear the brace in accordance with their treatment program and avoid over-use of the brace.

In one aspect, the apparatus described herein provides a wrist brace, including a flexible support casing having first and second longitudinal edges that are drawn together to enclose a user's wrist; a first plurality of securing loops, each having a lower rim and an upper rim, the lower rim being secured to the support casing and the upper rim extending outwardly from the support casing; at least one elastic securing member, having a first end, a second end and a middle portion, wherein the middle portion passes through at least one of the first plurality of securing loops without passing through the support casing; and a puller, attached to the first and second ends of the at least one elastic securing member, the puller being configured to adjustably tension the at least one elastic securing member with respect to the casing.

The securing loops are attached to the support casing in a position that makes them easily accessible to the elastic securing members. In one aspect, these components provide easier application of the wrist brace and more tailored contouring than conventional braces. In certain embodiments, the lower rims are secured to the support casing proximate the first edge. In certain embodiments, the upper rims extend outwardly from the first edge. The Securing loops may be molded in a unitary structure, wherein a plurality of loops are co-molded with a loop support portion. The loop support portion may be attached to the support casing.

In certain exemplary embodiments, the middle portion of the at least one elastic securing member passes through at least two of the first plurality of securing loops, thereby forming a loop opposite the puller. In certain embodiments, the wrist brace includes a plurality of elastic securing members wherein the first and second ends of each elastic securing member are attached to the puller.

The wrist brace may also include a second plurality of securing loops, each having a lower rim secured to the support casing and an upper rim extending outwardly from the support casing. In some such implementations, the middle portion of the at least one elastic securing member passes through at least one of the second plurality of securing loops. In certain embodiments, the middle portion of each elastic securing member passes through at least two of the second plurality of securing loops. As with the first plurality of securing loops, the second plurality of securing loops may also be molded in a unitary structure that is attached to the support casting. The second plurality of securing loops may be secured to the support casing proximate the second edge, and the upper rims may extend outwardly from the second edge.

In certain implementations, the first edge includes an edge of a removable pod unit connected to the support casing. The pod unit may be adjustably connected to the support casing. The first and/or second loop support portions may be secured to the support casing by a removable pod unit, and the first and/or second edges may include an edge of a removable pod unit. In certain implementations, the support casing comprises an inner layer constructed of a material that contours to the user's wrist. The material may be nylon foam. The support casing may extend along a user's arm to a position about mid-way between the user's elbow and wrist. The wrist brace may also include a strap that fits adjustably between a user's thumb and index finger.

BRIEF DESCRIPTION OF THE DRAWINGS

The foregoing and other objects and advantages will be appreciated more fully from the following further description thereof, with reference to the accompanying drawings wherein.

DETAILED DESCRIPTION

Described herein is a wrist support apparatus configured to provide adjustable and customizable support to a patient's wrist and lower arm. To provide an overall understanding of the apparatus, certain illustrative examples are herein described, and more particularly set forth in the figures. However, it will be understood by one of ordinary skill in the art that the apparatus described herein can be adapted and modified for other suitable applications, and that such other additions and modifications will not depart from the scope thereof.

Figure 1A:
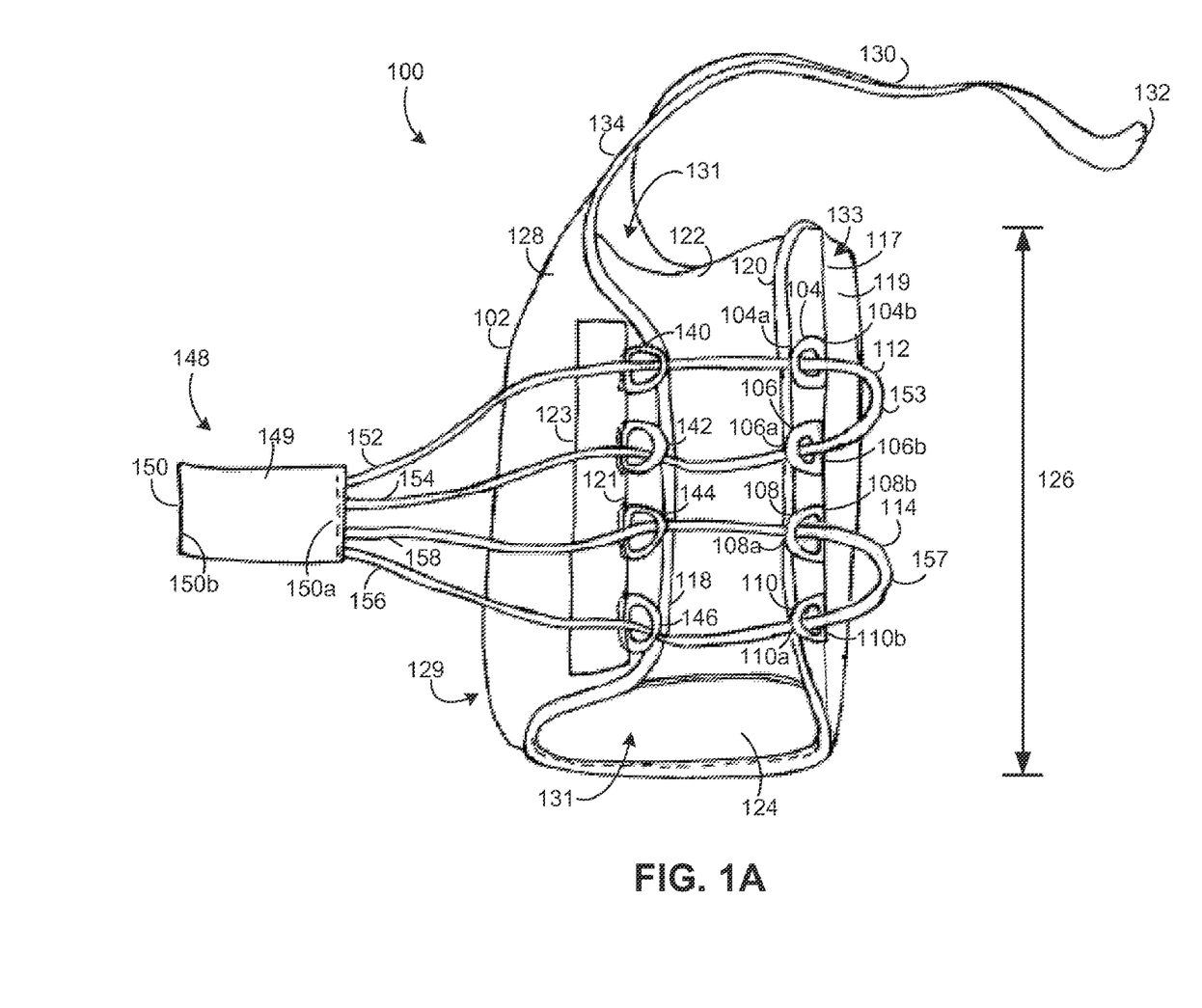
FIG. 1A is a view of a wrist brace including a support seam, prior to insertion of a user's wrist.

FIG. 1A is a view of a wrist brace 100, with a support seam 117, prior to insertion of a user's wrist. The wrist brace 100 includes a support casing 102, a first plurality of securing loops 104-110, a second plurality of securing loops 140-146, two elastic securing members 112 and 114 and a puller assembly 148. The wrist brace 100 in FIG. 1A is intended to be worn on a user's right arm, but construction of a left wrist brace is entirely analogous and is easily understood by one of ordinary skill in the art with the aid of this disclosure.

The support casing 102 includes a sheet of flexible support material 129 having two longitudinal edges 118 and 120. In use, a user's wrist is inserted into the wrist brace 100 and the two longitudinal edges 118 and 120 are drawn together, thereby closing the flexible support material 129 of the wrist brace 100 around the user's wrist. In use, the longitudinal edges 118 and 120 may overlap, or may remain spaced apart. A tongue 122 overlays the user's wrist and connects the two longitudinal edges 118 and 120 to create a sleeve 131 through which the user's arm protrudes. The user inserts the wrist into the wrist brace 100 via the sleeve 131 created by the combination of the support casing 102 and the tongue 122. The tongue 122 is constructed of any suitably flexible material (such as a polypropylene fabric, or nylon or cotton stockinette), which may also have advantageous properties such as breathability, moisture wicking, and cushioning. The tongue 122 is comprised of a single sheet of material, or may be comprised of multiple material sections or straps (such as a double layer of stockinette material). In some implementations, the wrist brace 100 does not include a tongue 122. In certain implementations, the tongue 122 is stitched to the support casing so that the seam is positioned between the tongue 122 and the support casing 102, thus avoiding any skin irritation that may result from direct contact between the skin and the seam. In certain implementations, the tongue 122 is attached to the support casing 102 at a first distance from the longitudinal edge 118 and a second distance, different from the first distance, from the longitudinal edge 120.

The support casing 102 is flexible, and is constructed of a layer or layers of materials of varying properties. In an embodiment, the support casing 102 includes an inner layer 124 positioned adjacent to a user's skin (or proximal to an adjacent layer). The inner layer 124 may include a material capable of contouring to a user's wrist, hand or arm. In an embodiment, the inner layer 124 includes a nylon foam. As discussed above with reference to the tongue 122, the material or materials comprising the inner layer 124 may also have advantageous properties such as breathability, moisture wicking and cushioning. The inner layer 124 may also include a region or regions for applying a medicament or other treatment to the user's skin. For example, the support casing 102 may include a pocket that holds a heat or cold source for applying heat or cold therapy to a user's skin. The heat or cold source may be integral or insertable into the support casing 102. One or more outer layers of support casing 102 may be made of any of a number of materials, including a felted or woven fabric, or a flexible plastic or other synthetic material. Additionally, the edges of support casing 102 may be finished (e.g., by sewing, gluing, fusing or another suitable finishing technique) or encased in a material such as a fabric or synthetic binding.

Figure 1B:
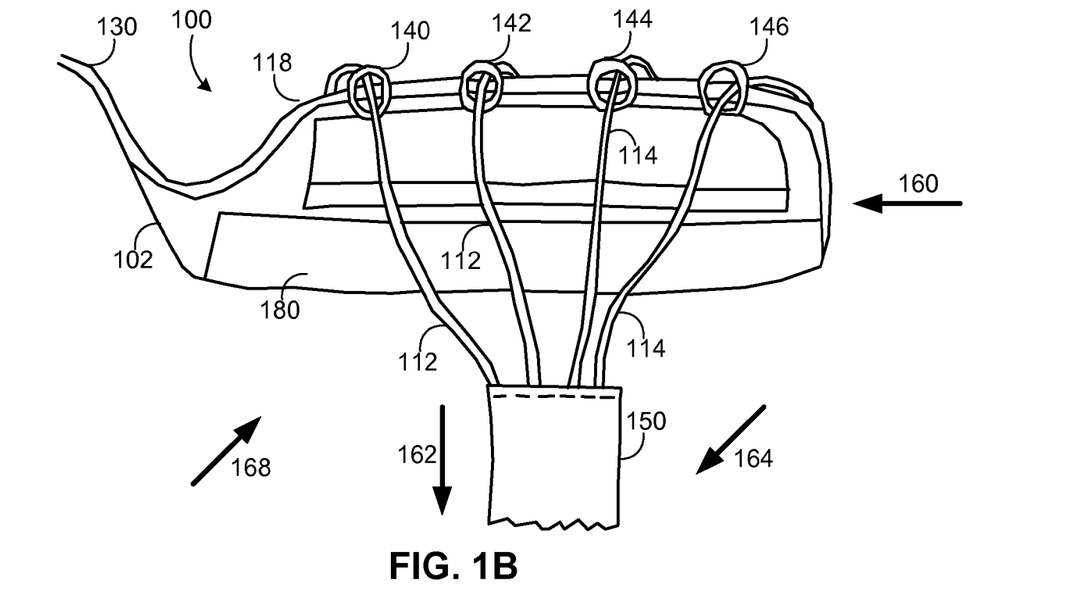
FIGS. 1B-1C are medial and lateral side views of the wrist brace of FIG. 1A.

Support casing 102 may also include pockets between or within the layers for stiff support inserts which may provide additional support to a user's hand or wrist. For example, the wrist brace 100 may include a palmer stay pocket 180 (FIG. 1B). In certain implementations, a palmer stay is made of metal or stiff plastic, and is inserted into the longitudinal palmer stay pocket 180 in the support casing 102. The palmer stay may be customized or contoured to fit a user's arm and wrist (e.g., with a bend in the stay positioned to support a user's palmer crease, and aligned with the user's forearm). Additional foam padding may be included in the support casing between the palmer stay and the user's skin, and the palmer stay may have rounded edges and corners to avoid damaging the soft goods of the wrist brace 100 and to reduce the risk of accidentally injuring a user. The palmer stay may be permanently installed in the wrist brace 100, or may be removable from the wrist brace 100. In certain implementation, the palmer stay is snugly encased in a pocket of the support casing 102, with an opening at the bottom of the palmer stay pocket 180 proximal to the user's forearm. This opening may be adjustably closed by a piece of hook and loop material, or any other suitable mechanism.

As another example of a stiff support insert, the wrist brace 100 may include a longitudinal dorsal stay, instead of or in addition to a palmer stay. In certain implementations, the dorsal stay is a flat member made of metal or stiff plastic, which can be customized and bent to the user's therapeutic requirements and also provide sufficiently rigid support during use. In certain implementations, the dorsal stay is snugly encased in a dorsal stay casing 182 (FIG. 1D) that is adjustably attachable to the support casing 102. The dorsal stay casing 182 includes a strip of loop material and a strip of hook material secured "back-to-back," such that, in use, the hook side of the hook material attaches to the outer surface 128 of the support casing 102, the loop side of the of loop material faces away from the outer surface 128, and the dorsal stay is sandwiched between the hook material and the loop material. In certain implementations, the strip of loop material includes the same material used in at least a portion of the outer surface 128 of the support casing 102. When the outer surface 128 includes a material that engages with the hook side of the hook material, the entire dorsal stay assembly, including the dorsal stay and the dorsal stay casing 182, can be adjustably positioned on and secured to the outer surface 128 of the support casing 102. The position of the dorsal stay assembly can be adjusted to provide customized support and fit for a particular user, and in particular, can be adjustably positioned proximally and distally to achieve a desired control of the user's range of wrist motion. The dorsal stay assembly can also be removed completely from the wrist brace 100, for example, when a user is in a rehabilitation phase of treatment. The contact surface area between the dorsal stay casing 182 and the outer surface 128 can be selected to provide a secure connection so that the dorsal stay assembly remains in the desired position when longitudinal and lateral forces are exerted on the wrist brace 100 during normal use. Since the dorsal stay assembly is positioned on the outer surface 128 of the support casing 102, the risks of undesirable friction and compression between the dorsal stay assembly and the user's skin are reduced. Moreover, the sandwich construction of the dorsal stay assembly has a low profile, reducing the risk that the dorsal stay assembly or the wrist brace 100 will catch or snag on objects in the user's environment.

The support casing 102 has a longitudinal length 126. Different embodiments of the wrist brace 100 may differ in the longitudinal length 126, depending upon the physiological condition of a user and the type of support desired. The longitudinal length 126 may be chosen so that the wrist brace 100 extends along a user's arm to a position about mid-way between the user's elbow and wrist. This length may provide advantageous support to a user's hand and wrist by providing supportive forces from the user's forearm.

The support casing 102 also includes an outer surface 128. As discussed in additional detail below, the outer surface 128 includes an attachment region 133 which includes connective material, such as hook-and-loop material, to attach various elements of the wrist brace 100. The attachment region 133 of the outer surface 128 may include a connective material capable of adjustable attachment to at least one other element of the wrist brace 100. In an embodiment, an attachment region 133 of the outer surface 128 includes any one or more of a snap, fastener, buckle, tie, spring clip, bandage clip, cleat, zipper, button or adhesive. An attachment region 133 of the outer surface 128 may be capable of attachment to more than one element of the wrist brace 100, as discussed in additional detail below.

As shown in FIG. 1A, the support casing 102 also includes a strap 130. In use, the strap 130 fits between a user's thumb and index finger. The strap 130 may be constructed of any suitable material, including materials that provide reduced irritation due to friction. A first end 132 of the strap 130 attaches to the support casing 102. This attachment may be adjustable, for example, by attaching the first end 132 to an attachment region of the outer surface 128 as discussed above. In an embodiment, the first end 132 of the strap 130 is adjustably attachable to more than one location on the wrist brace 100, as discussed in additional detail below. By the adjustable attachment of the strap 130, the wrist brace 100 can be adjusted to fit users with different physiological dimensions, as well as users participating in different types of manual activity. Additionally, adjustment of the elements of the wrist brace 100, including the strap 130, provides different supportive forces to the arm, wrist and hand to achieve different preventative and/or therapeutic goals. As illustrated in FIG. 1A, the strap 130 is a continuous extension of the support casing 102. The strap 130 may have a narrowing between the first end 132 and the second end 134 to more comfortably seat the strap 130 between the user's thumb and index finger during use. The strap 130 may include a separate connector portion (not shown), which may be a strip of hook material stitched to the end of the strap 130 and which is attachable to the outer surface 128 of the support casing 102.

In an embodiment, the strap 130 is attachable to the support casing 102 at a second end 134 by any of the attachment methods described herein.

The wrist brace 100 includes a first plurality of securing loops 104-110. As depicted in FIG. 1A, the securing loops 104-110 are attached to the outer surface of the support casing 102, for example, along the support seam 117 between a support strip 119 and the outer surface 128 and proximal to the longitudinal edge 120. The securing loops may also be fastened directly to the support casing 102 without a support seam 117.

In an embodiment, the securing loops 104-110 are permanently attached to the support casing 102 via the support seam 117. The support seam 117 reinforces the attachment of the securing loops 104-110 to the support casing 102. The support seam may be a sewn seam, a glued seam, a fused seam, or any other method of attachment within a layer of the support casing 102 or between layers of the support casing 102. In an embodiment, the support seam 117 is a sewn seam connecting the inner layer 124 to an outer layer of the support casing 102. The support seam may include a support strip 119, which may be sewn, glued, fused, or otherwise permanently and securely attached to the support casing 102. Exemplary support strips are constructed of a sturdy material suitable for anchoring the securing loops 104-110 to the support casing, and may also include stiffening members (e.g., stays) for providing additional rigid or semi-rigid support to the user's wrist. The four securing loops 104-110 depicted in FIG. 1A represent an illustrative number and arrangement of a first plurality of securing loops, and embodiments may include any number and arrangement of securing loops and may be spaced at equal or unequal intervals along a longitudinal edge 120 of the wrist brace 100. Support strips are discussed in additional detail below.

Each of the securing loops 104-110 is secured to and extends outwardly from the wrist brace 100. As shown, the securing loops each are secured to the support casing 102 near a lower rim, leaving a free upper rim, the upper rims of the securing loops thus being in an elevated position relative to the support casing 102. As discussed above, the outward extension and elevated position of the securing loops 104-110 provides for greater ease of adjustment than the embedded eyelets of conventional braces and reduces uneven pressure when the brace is in use. Additionally, the use of securing loops, such as the securing loops 104-110, may reduce undesirable friction between various elements of the wrist brace (e.g., friction between the securing members 112 and 114 and the support casing 102 or the tongue 122). These improvements may result in a number of benefits, including improved user compliance due to reduced irritation and increased durability of the wrist brace 100.

Figure 4A:
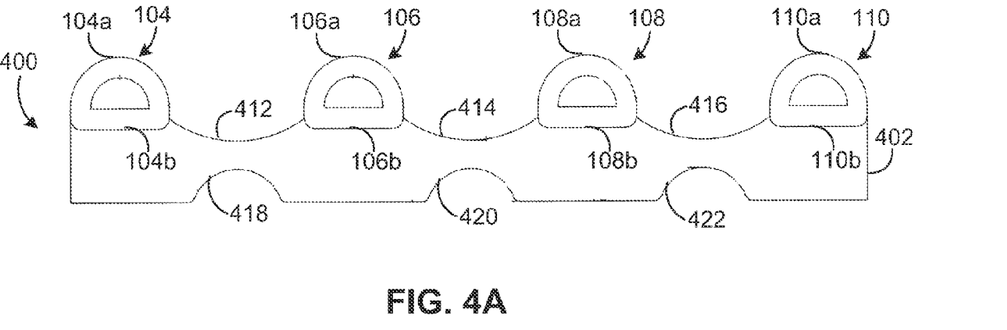
FIGS. 4A-4B are plan and elevation views, respectively, of a loop structure.
Figure 4B:
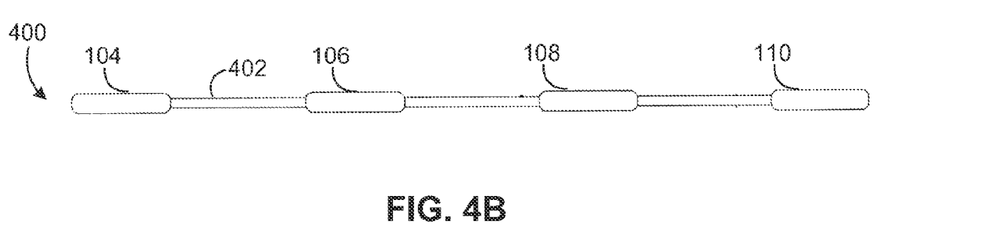
Figure 5:
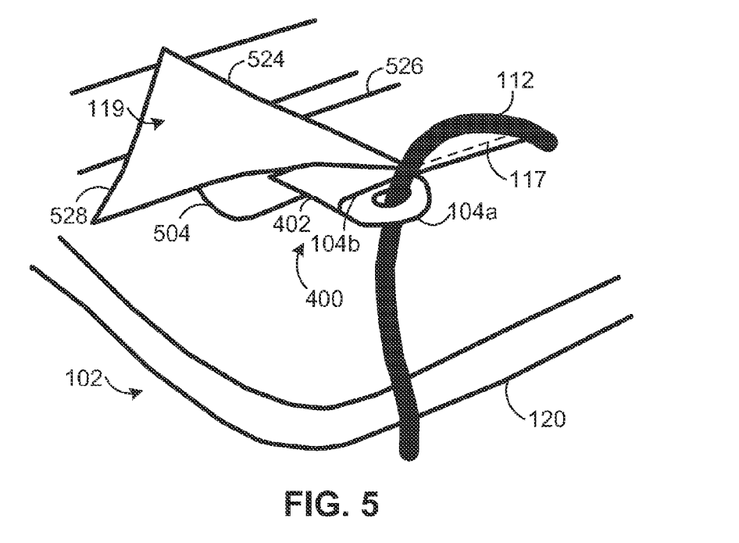
FIG. 5 is a deconstructed view of layers of a wrist brace assembly proximate to a longitudinal edge.

A securing loop may be constructed from any of a number of materials, including rigid or semi-rigid plastic, metal, textile or woven material, or a combination thereof. For example, a securing loop may be a rigid plastic D-shaped loop. Conventional metal eyelets, as used in existing braces, would tear the material of the support casing 102 and would leave metal edges exposed to the patient's skin when mounted in the manner illustrated in FIG. 1A, and are thus not readily adapted for use as the securing loops described herein, The material or materials included in a securing loop are selected based on the material included in a securing member (e.g., the securing members 112 and 114) to provide complementary functional benefits, as discussed further below. In an embodiment, different securing loops are constructed of different materials and/or are different shapes. A securing loop is attached to the wrist brace 100 (e.g., to the outer surface 128 of the support casing 102) by any of a number of attachment methods, including embedding in a seam, a sewn attachment, an intermediate connector, gluing, fusing, and stapling, to name a few. In particular, the securing loops 104-110 have lower rims 104b-110b that are permanently secured to the wrist brace 100, such as by stitching or gluing near or on the lower rims 104b-110b. The loops have upper rims 104a-110a that extend from the surface of the support casing 102 in a free, elevated position relative to the support casing 102, providing freer access to the securing members 112 and 114 than is provided in prior art devices having embedded eyelets. Additionally, the lower rims 104b-110b are secured to the wrist brace 100 away from the longitudinal edge 120, so that the securing loops 104-110 do not extend beyond the longitudinal edge 120. In certain implementations, the securing loops are each separately secured to the brace. In alternative implementations, the securing loops are co-molded as a unitary structure with a loop support portion. An example is shown in FIGS. 4A-4B and 5, described below.

The wrist brace 100 further includes two securing members 112 and 114. The securing member 112 includes a first end 152, a second end 154 and a middle portion 153, and the securing member 114 includes a first end 156, a second end 158 and a middle portion 157. Each of the middle portions 153 and 157 of the securing members 112 and 114, respectively, passes through at least two of the securing loops 104-110. As shown, the middle portion 153 of the securing member 112 forms a loop that spans between and passes through the securing loops 104 and 106, and the middle portion 157 of the securing member 114 forms a loop that spans between and passes through the securing loops 108 and 110. The securing members 112 and 114 are each an elastic member, such as an elastic cable, an elastic strip, a rubber or stretchable synthetic, or a transparent elastic, and may include portions that are braided, knitted or woven. In an embodiment, a securing member includes an elastic blend. The cross-section of each of the securing members may be any of a number of shapes, including circular, oval, flat, tubular, or any suitable shape. The cross-sectional shape and/or material composing a securing member may be chosen to be complementary to the shape and/or material composing a securing loop, for example, to reduce undesirable frictional contact between the securing member and securing loop when a user adjusts the wrist brace 100. A complementary design of securing member and securing loop shape and/or material may provide improved friction characteristics that provide a comfortable fit and help prevent shifting of the wrist brace 100 when secured to a user.

The wrist brace 100 further includes a second plurality of securing loops 140-146. As illustrated in FIG. 1A, the second plurality of securing loops 140-146 are attached to the support casing 102 along the edge of support seam 121 between the support strip 123 and the support casing 102, and proximal to the longitudinal edge 118. The support seam 121 and the attachment of the securing loops 140-146 may take the form of any of the attachments described herein for the support seam 117 and the securing loops 104-110. For example, as shown, the second plurality of securing loops have upper rims that extend outwardly from and are secured in an elevated position relative to the support casing 102 and the longitudinal edge 118. Such embodiments provide improved ease of access and use, as described above. Further, the support strip 123 may include any of the support strip features described herein.

The securing loops 140-146 are constructed in accordance with the embodiments described above with reference to the securing loops 104-110. In use, the middle portion of each of the securing members 112 and 114 spans between and passes through at least one of a second plurality of securing loops. As shown in FIG. 1A, the middle portion 153 of the securing member 112 passes through the securing loops 140 and 142 and the middle portion 157 of the securing member 114 passes through the securing loops 144 and 146. The four securing loops 140-146 depicted in FIG. 1A represent an illustrative number and arrangement of a second plurality of securing loops, and embodiments may include any number and arrangement of securing loops as discussed above with reference to the first plurality of securing loops 104-110. In certain embodiments, the number of securing loops used in the first plurality of securing loops is different from the number of securing loops used in the second plurality of securing loops.

The wrist brace 100 also includes a puller assembly 148. The puller assembly 148 includes the securing members 112 and 114 and a puller 150. The puller 150 includes a proximal end 150a and a distal end 150b. As shown in FIG. 1A, the first ends 152 and 154 and the second ends 156 and 158 of the securing members 112 and 114, respectively, are attached to the puller 150 at the proximal end 150a. This attachment could be performed by any of a number of methods, including embedding an end of a securing member in a seam, a sewn attachment, a glued or fused attachment, an intermediate connector, or any other suitable attachment method. The puller 150 is used to adjustably tension the securing members 112 and 114. The attachment between the first ends 152 and 156 and the second ends 154 and 158 and the proximal end 150a of the puller 150 is sufficient to withstand the adjustable tensioning forces applied to the securing members 112 and 114 when the wrist brace is in use. Additionally, the puller 150 is constructed of one or more layers of durable material that can withstand the forces exerted on the proximal end 150a of the puller 150 by the securing members 112 and 114 and the forces exerted on the distal end 150b of the puller 150 by the user when using the puller 150 to adjust the wrist brace 100 during use.

A surface of the puller 150 includes an attachment region for connecting to an attachment region of the outer surface 128 of the support casing 102. For example, a surface of the puller 150 may include a region of hook-and-loop material capable of attachment to a complementary region of the outer surface 128 (such as the attachment region 133). By the adjustable attachment of the puller 150, the wrist brace 100 can be further adjusted to fit users with different physiological dimensions, as well as users participating in different types of physical activity. The adjustability of the connection between the puller 150 and the support casing 102 may be selected based on hook-and-loop dimensions. For example, a large region of hook-and-loop material included in the attachment region 133 on the outer surface 128 may allow for more possible locations and orientations of the connection between the puller 150 and the outer surface 128 than a small region of hook-and-loop material. Additionally, the location of the attachment regions on each of the puller 150 and the support casing 102 (e.g., the attachment region 133) provides constraints on the adjustability of the connection between the puller 150 and the support casing 102. In certain implementations, substantially all of the outer surface 128 of the support casing 102 is included in the attachment region 133. Attaching the puller 150 to different attachment regions (e.g., the attachment region 133) of the support casing 102 provides different therapeutic benefits to a user of the wrist brace 100 by enabling the application of different forces via the tension of the securing members, discussed in additional detail below.

A puller, such as the puller 150, may also include attachment regions on multiple faces to allow the puller to attach to the support casing 102 in different orientations. Such attachment regions may allow multiple elements of the wrist brace 100 to attach in varying configurations according to a user's preferences and goals. In an embodiment, the puller 150 includes an attachment region on the face of the puller 150 opposite the attachment region 149 to enable both faces to attach to the support casing 102 and achieve the first and second support configurations described below, for example. The puller may also include attachment regions to which the strap 130 of the wrist brace 100 may attach.

The puller 150 is designed to be grasped and manipulated by a user, as discussed below. The puller 150 may take any of a number of suitable shapes, including a rectangle, a loop, or any curved shape. In certain implementations, the distal end 150b of the puller 150 is rounded. The puller 150 may be largely planar or substantially three-dimensional (e.g., a cylinder or rectangular solid), and may include any of a number of design elements for ergonomic use in the manner described below. In certain implementations, the puller 150 is constructed as layers of different materials, including a hook-and-loop material as described above, and has a low profile to avoid catching or snagging on objects in the user's environment when the wrist brace 100 is in use.

Figure 1C:
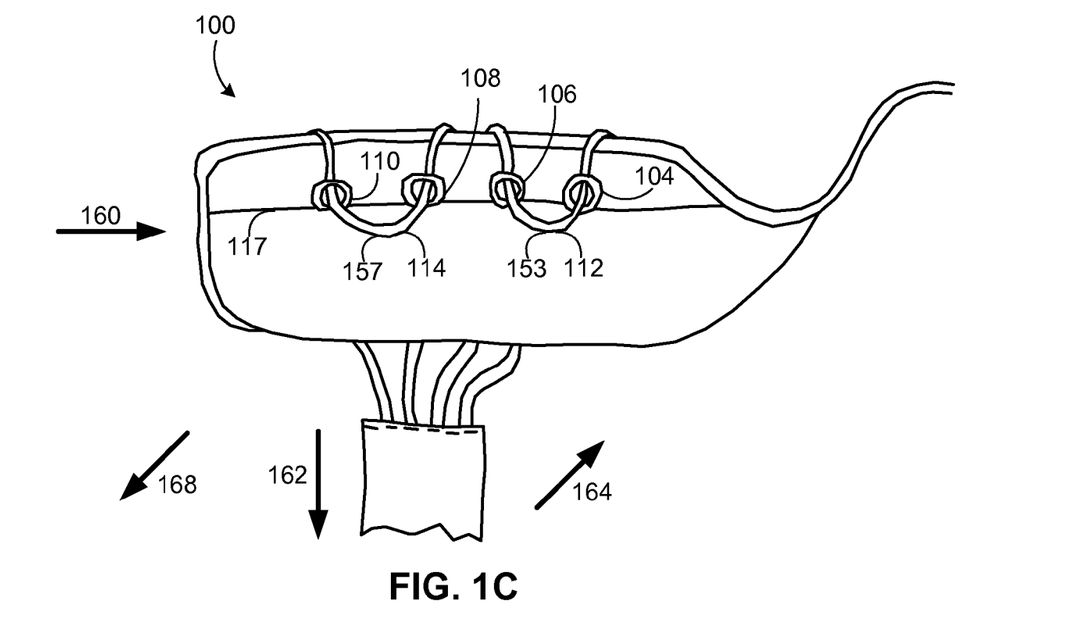

FIGS. 1B-1C are medial and lateral side views of wrist brace 100. The position and orientation of the support seams 117 and 121 are positioned to be therapeutically-suitable. When a user's wrist is inserted in the support casing 102 (e.g., by inserting the hand in the direction of the arrow 160), the support casing 102 will substantially enclose the user's wrist. The strap 130 is adjustably attached to another portion of the wrist brace 100, for example, the support casing 102. When attached, the strap 130 is strapped to the support casing 102 in position between a user's thumb and forefinger, helping secure the wrist brace 100 to the user's arm by reducing relative motion between the wrist brace 100 and the user's arm in both the longitudinal and transverse directions. The location of the point of attachment may be adjustable to accommodate differently-proportioned users, and may be selectively unattached.

Applying a force to the puller 150 in the direction of the arrow 162 (i.e., outwardly from the wrist brace 100) will increase the tension on the elastic securing members 112 and 114. Changing the direction and magnitude of the applied force will adjust the tension of the securing members. A desired tension on each of the securing members 112 and 114 (including magnitude and direction) is achieved by the attachment of the puller 150 to the support casing 102. As shown, the puller 150 is attached to the outer surface of the support casing 102. In a first support configuration, a force is applied in the direction of the arrow 162, then in the direction of the arrow 168 in order to "wrap" the securing members 112 and 114 around the user's wrist, whereupon the puller 150 is attached to the support casing 102 to secure the brace to the wrist. In use, the elastic securing members 112 and 114 mold around the wrist and securely fasten the brace. The elasticity of the securing members thus provides a more adjustable fit than is provided by braces that use conventional shoelace-type straps.

Figure 1D:
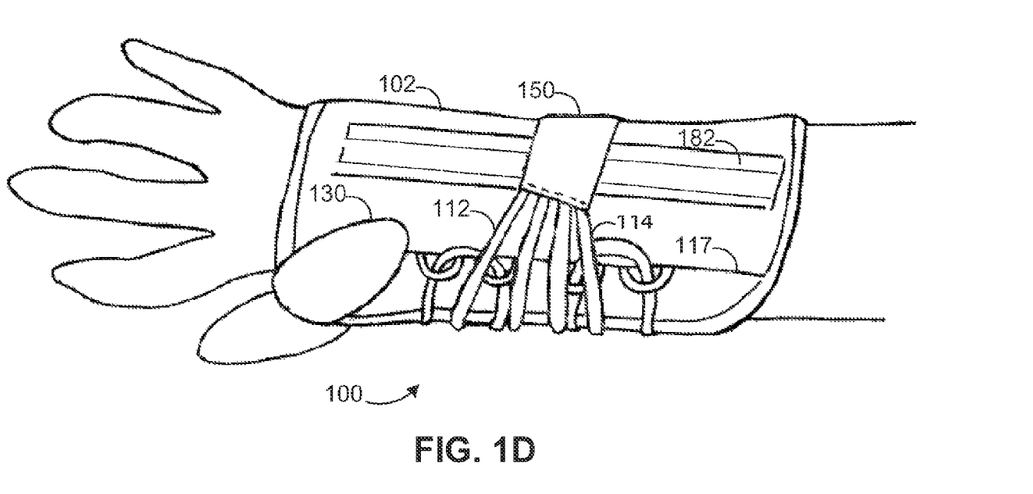
FIG. 1D is a perspective view of a wrist brace in a support configuration on a user's wrist.

FIG. 1D is a perspective view of a wrist brace 100 in a preferred second support configuration on a user's wrist. To configure the wrist brace 100 in this second support configuration (different from the first configuration described above), a force is applied in the direction of the arrow 162, then in the direction of the arrow 164 in order to tension the securing members 112 and 114 by "folding" them back upon themselves, whereupon the puller 150 is attached to the support casing 102. FIG. 1D is a perspective view of a wrist brace 100 in this second support configuration on a user's wrist. As shown, the puller 150 tensions the securing members 112 and 114, then attaches to the support casing 102 to maintain the securing members 112 and 114 in a tensioned state. In the configuration depicted in FIG. 1D, both the puller 150 and the strap 130 are attached to the wrist brace 100 at various points on the outer surface of the support casing 102, as is a pod unit (not shown). In embodiments that include multiple pullers (e.g., the pullers 300-304 depicted in FIGS. 3A-3D, respectively), the pullers may attach, separately and spaced apart, to the other components of the wrist brace 100 described herein.

Figure 2A:
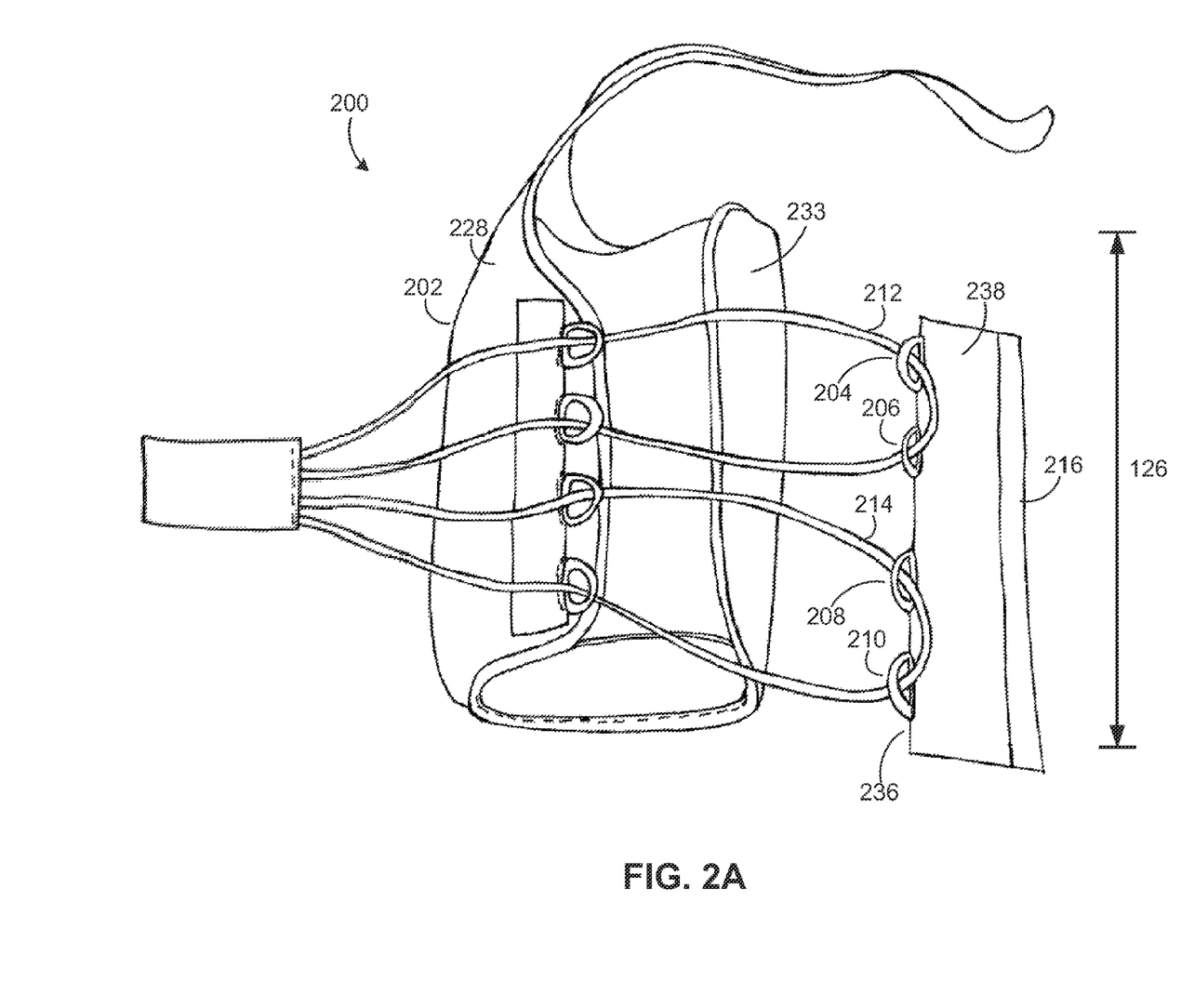
FIG. 2A is a view of a wrist brace including a pod unit, prior to insertion of a user's wrist.

FIG. 2A is a view of a wrist brace 200 including a pod unit 216, prior to insertion of a user's wrist. As depicted in FIG. 2A, the securing loops 204-210 are secured to the pod unit 216 along a longitudinal edge 236. The securing loops 204-210 extend outwardly from the pod unit 216. In an embodiment, securing loops secured to a pod unit are in an elevated position relative to the surface and/or edge of the pod unit. The securing members 212 and 214 pass through the securing loops in the manner described above with reference to FIG. 1A. In FIG. 2A, the pod unit 216 is depicted as separated from the support casing 202 for illustrative purposes. When the wrist brace 200 is in use, the pod unit 216 is attached to the support casing 202. The pod unit 216 is attachable to the outer surface 228 of the support casing 202. In an embodiment, the pod unit 216 is adjustably connected to the support casing 202. The adjustable connection of the pod unit 216 to the support casing 202 in the wrist brace 200 may include an adjustable position, an adjustable orientation, or a combination of the two. A surface of the pod unit 216 includes an attachment region for connecting to an attachment region of the outer surface 228 of the support casing 202. For example, a surface of the pod unit 216 (facing the support casing 202, opposite the outer pod surface 238) includes a region of hook-and-loop material capable of attachment to a complementary region of the outer surface 228 (such as the attachment region 233). By the adjustable attachment of the pod unit 216, the wrist brace 200 can be further adjusted to fit users with different physiological dimensions, as well as users participating in different types of manual activity, as described above with reference to the adjustable attachment of the puller 150 to the support casing 102 in the wrist brace 100 of FIGS. 1A-1D.

In an alternate embodiment, a pod unit 216 is permanently fixed to the support casing 202 of the wrist brace 200, for example, by stitching, stapling or gluing, and may serve to provide a support seam or strip (such as support seam 117 or support strip 119 of the wrist brace 100.) In embodiments that employ a permanent support seam, such as the wrist brace 100, or a permanently fixed pod unit (e.g., the pod unit 216), the elasticity of the securing members provides sufficient adjustability for most users.

Figure 2B:
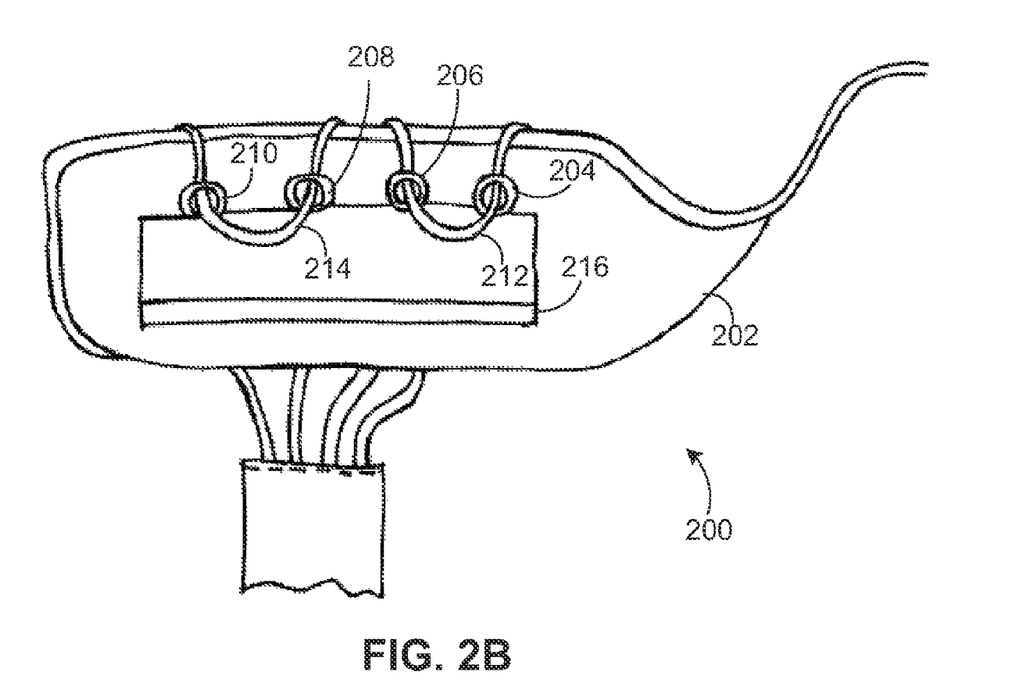
FIG. 2B is a lateral side view of the wrist brace of FIG. 2A.

The lateral side view of wrist brace 200 depicted in FIG. 2B illustrates a configuration in which a pod unit 216 is attached to the support casing 202. This attachment may be in accordance with any of the attachment mechanisms described herein, including a permanent attachment or an adjustable attachment. The position of the pod unit 216 on the support casing is purely illustrative. In an embodiment, the pod unit is capable of placement at multiple locations and in multiple orientations with respect to the support casing 202 in the wrist brace 200.

FIGS. 3A-3D are views of puller assemblies 300-306 that may be used with the braces described above. The puller assemblies 300-306 are each configured to be used in any of the wrist braces described herein. Each of the puller assemblies 300-306 includes at least one puller and at least one securing member, which may be individually constructed and attached together in accordance with any of the embodiments described herein, including those described above for puller assembly 148, puller 150 and securing members 112 and 114.

Figure 3A:
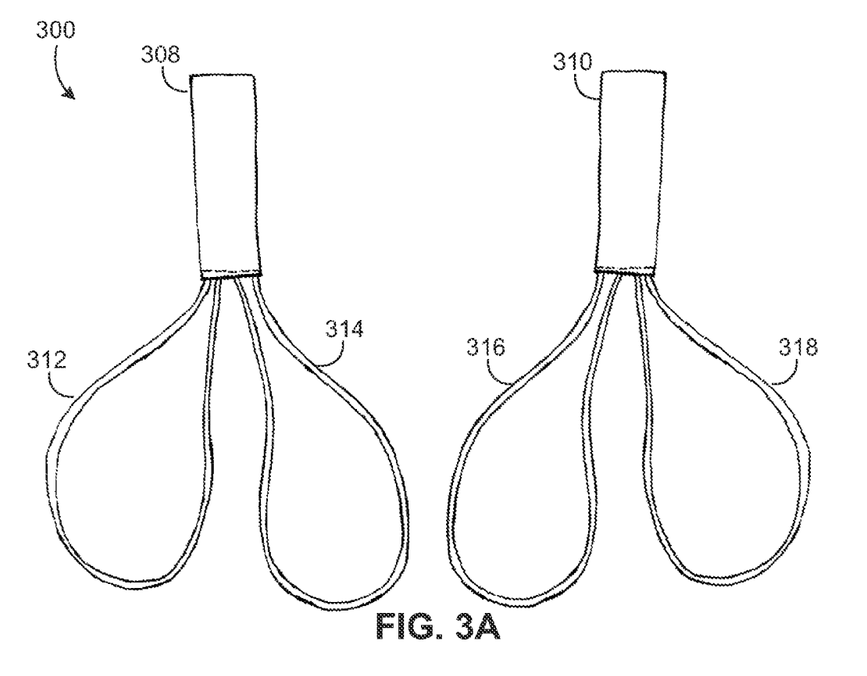
FIGS. 3A-3D are views of puller assemblies.

FIG. 3A depicts a puller assembly 300 which includes two pullers 308 and 310 and four securing members 312-318. Each of the securing members 312 and 314 is attached at both ends to the puller 308, and each of the securing members 316 and 318 is attached at both ends to the puller 310. The puller assembly 300 may be used instead of, or in addition to, the puller assembly 150 in the wrist brace 100. In an embodiment, the four securing members 312-318 each pass through one of the securing loops 104-110. The choice of which securing member passes through which securing loop depends upon the support forces desired to achieve a user's therapeutic goals.

Figure 3B:
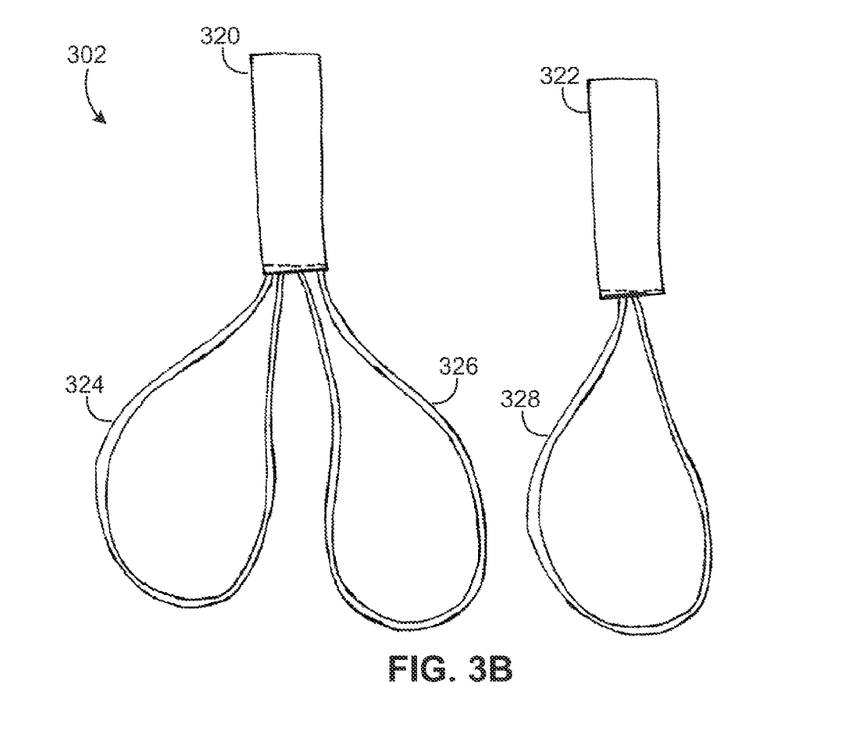

FIG. 3B depicts a puller assembly 302 which includes two pullers 320 and 322 and three securing members 324-328. Both ends of the securing members 324 and 326 are attached to the puller 320 and both ends of the securing member 328 are attached to the puller 322. Each of the securing members 324-328 is capable of being passed through at least one securing loop to tension a wrist brace in the manner described above with reference to the securing members 112 and 114.

Figure 3C:
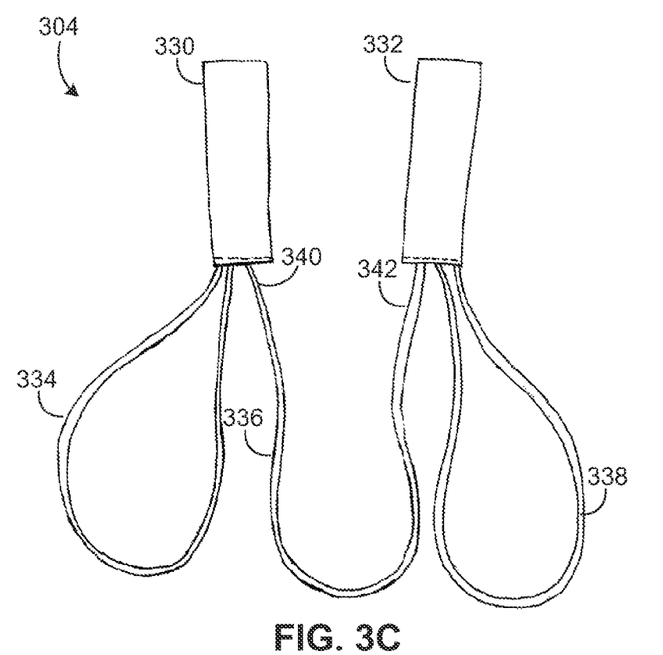

FIG. 3C depicts a puller assembly 304 which includes two pullers 330 and 332 and three securing members 334-338. Both ends of the securing member 334 are attached to the puller 330, and both ends of the securing member 338 are attached to the puller 332. A first end 340 of the securing member 336 is attached to the puller 330, and a second end 342 of the securing member 336 is attached to the puller 332.

Figure 3D:
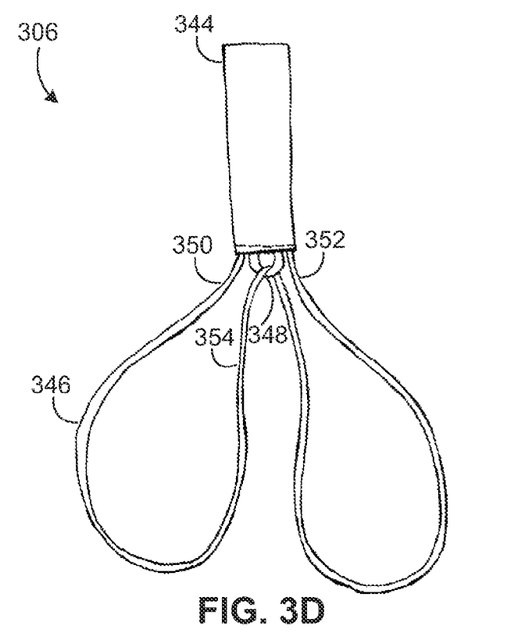

FIG. 3D depicts a puller assembly 306 which includes a puller 344, a securing member 346 and a puller loop 348. The puller loop 348 may be constructed of a rigid plastic or metal material, or a flexible material, and may take the form of any of the securing loops described herein. The first end 350 of the securing member 346 and the second end 352 of the securing member 346 are permanently attached to the puller 344. This attachment may take the form of any of the attachment techniques described above with reference to puller 150 and securing members 112 and 114. The middle portion 354 of the securing member 346 passes through the puller loop 348. The puller loop 348 and its attachment to the puller 344 may take the form of any of the attachment techniques described above with reference to the securing loops 104-110. In use, the middle portion 354 is capable of sliding within puller loop 348 as the direction of the tensioning force applied to the securing member 346 by the puller 344 is changed, which changes the distribution of the supportive forces applied by the brace to the user's wrist. A puller may also include more than one puller loop.

As described above, securing loops, such as the securing loops 104-110 of the wrist brace 100 (FIG. 1A), the securing loops 140-146 of the wrist brace 100 (FIG. 1A), and/or the securing loops 204-210 of the wrist brace 200 (FIG. 2A), may be co-molded as a unitary structure with a loop support portion. FIGS. 4A-4B depict plan and elevation views, respectively, of a loop structure 400 joining the securing loops 104-110 with a loop support portion 402. The loop structure 400 may be made of one or more durable and flexible materials, such as nylon or another plastic, and may be constructed by molding or other machining. The loop structure 400 may be co-extruded or co-molded into a unitary piece. In certain embodiments, the loop support portion 402 is made of a nylon plastic capable of being stitched through. The securing loop side of the loop support portion 402 includes the indentations 412-416, and the opposite side of the loop support portion 402 includes the indentations 418-422.

The shape and structure of the loop support portion 402, including the size and location of the securing loops 104-110, the indentations 412-416 and the indentations 418-422, improves the flexibility and reduces the weight and amount of material of the loop structure 400. The loop support portion 402 has a length that is sized to span the longitudinal distance approximately from a user's wrist to the middle of a user's forearm, and to space the securing loops 104-110 approximately equally along that length. In certain implementations, the length of the support portion 402 (i.e., the distance from the end nearest the securing loop 104 to the end nearest the securing loop 110) is in the range of approximately 6 cm to approximately 15 cm. The length of the support portion 402 is sufficient to allow the tensioning forces from the securing members to provide support to a therapeutically-appropriate span of the user's wrist and forearm. In certain implementations, the longitudinal spacing between the centers of each of the securing loops 104-110 is in the range of approximately 15 mm to approximately 60 mm. The longitudinal spacing of the securing loops is selected based on the length of the wrist brace, the distance over which the brace is to be tightly secured to the user's arm and wrist by the securing members, and the number of securing loops desired. In certain implementations, the outer radius of each of the securing loops 104-110 is in the range of approximately 3 mm to approximately 11 mm, and the inner radius of each of the securing loops 104-110 is in the range of approximately 2 mm to approximately 8 mm. The dimensions for the inner and outer radii of the securing loops 104-110 are selected to be complementary to the dimensions of the securing members (e.g., the securing members 112 and 114 of FIG. 1A). In certain implementations, the first indentations 412-416 have radii in the range of approximately 8 mm to approximately 24 mm. In certain implementations, the second indentations have radii in the range of approximately 2 mm to approximately 12 mm.

In certain implementations, the loop structure 400 is included in the wrist brace 100 according to the sandwich construction illustrated in FIG. 5, which depicts a semi-exploded view of the support casing 102 of FIG. 1, including the securing loop 104 and a portion of the longitudinal edge 120. A surface of the support casing 102 is overlaid with a stay member 504, the loop structure 400, and the support strip 119. The stay member 504 is a rigid or semi-rigid longitudinal support, and may take the form of any of the stays described herein or known in the art. To assemble the wrist brace 100 in accordance with the construction illustrated in FIG. 5, a first longitudinal edge 524 of the support strip 119 is attached to the support casing 102 (e.g., via stitching). A second longitudinal edge 526 of the support strip 119 is attached to the support casing 102 by stitching a linear support seam 117 through the support strip 119 and the loop support portion 402. A third edge 528 of the support strip 119 may be attached to the support casing 102, or may be left open to allow the stay member 504 to be removed or repositioned (the same is true for the edge of the support strip 119 opposite to the third edge 528, not shown).

When assembled, the lower rim 104*b* of the securing loop 104 is secured to the support casting 102 via the loop support portion 402, and the upper rim 104*a* extends outwardly from the support seam 117 and the support casing 102. The stay member 504 is snugly secured in the pocket created between the support strip 119 and the support casing 102. The indentations 412-416 (FIG. 4A) allow the support seam 117 to go through the material of the support portion 402 for the sections of the support seam 117 proximal to one of the securing loops 104-110, but not go through the support portion 402 for the sections of the support seam 117 not proximal to one of the securing loops 104-110 (i.e., when the support seam 117 is between two securing loops). The support seam 117 thus alternatingly stitches the support portion 402 directly to the support strip 119 and the support casing 102, and encases the support portion 402 between the support strip 119 without stitching into the support portion 402. This construction helps maintain a tight and substantially flat interface between the second longitudinal edge 526 of the support strip 119 and the support casing 102, reducing the risk of catching or snagging the wrist brace 100 or abrading a user if the second longitudinal edge 526 were elevated from the support casing 102. Securing the loop support portion 402 to the support casing 102 may be advantageous over implementations in which the securing loops 104-110 are each attached directly and separately to the support casing. In use, the loop support portion 402 absorbs the torsional forces exerted on the securing loops 104-110 by the securing member 112 instead of translating these forces directly to the support casing 102, which may weaken the connection (e.g., stitching or adhesive) between the securing loops 104-110 and the support casing 102. Replacing multiple separate loops with a single loop structure 400 improves the manufacturability of the wrist brace 100. Although FIGS. 4A-4B and 5 have been described with reference to the securing loops 104-110 of the wrist brace 100, loop support structures like the loop structure 400 may also be used to provide the securing loops 140-146 of the wrist brace 100 (FIG. 1A), and the securing loops 204-208 of the wrist brace 200 (FIG. 2A).

It is to be understood that while certain forms of the wrist brace have been illustrated and described herein, it is not to be limited to the specific forms or arrangement of parts described and shown. Those skilled in the art will know or be able to ascertain using no more than routine experimentation, many equivalents to the embodiments and practices described herein. Accordingly, it will be understood that the invention is not to be limited to the embodiments disclosed herein.

What is claimed is:

1. A wrist brace, comprising:
   a flexible support casing including first and second longitudinal edges that are drawn together to enclose a user's wrist;
   a first plurality of securing loops, each having a lower rim and an upper rim, the lower rim being secured to the support casing and the upper rim extending outwardly from the support casing;
   at least one elastic securing member having a first end, a second end and a middle portion, wherein the middle portion passes through at least one of the first plurality of securing loops without passing through the support casing; and
   a puller, attached to the first and second ends of the at least one elastic securing member, the puller being configured to adjustably tension the at least one elastic securing member with respect to the casing.

2. The wrist brace of claim 1, wherein the lower rims of the first plurality of loops are secured to the support casing proximate to the first edge.

3. The wrist brace of claim 2, the upper rims of the first plurality of loops extending outwardly from the first edge.

4. The wrist brace of claim 1, wherein a first loop support portion joins the first plurality of loops into a unitary structure.

5. The wrist brace of claim 4, wherein securing a lower rim of each of the first plurality of securing loops to the support casing comprises securing the lower rim to the first loop support portion, and securing the first loop support portion to the support casing.

6. The wrist brace of claim 4, wherein the first edge comprises an edge of a removable pod unit connected to the support casing and the first loop support portion is secured to the support casing by the removable pod unit.

7. The wrist brace of claim 1, further comprising a second plurality of securing loops, each having a lower rim and an upper rim, the lower rim being secured to the support casing and the upper rim extending outwardly from the support casing.

8. The wrist brace of claim 7, the lower rims of the second plurality of loops being secured to the support casing proximate the second edge.

9. The wrist brace of claim 7, further comprising a second loop support portion that joins the second plurality of loops into a unitary structure.

10. The wrist brace of claim 9, wherein securing a lower rim of each of the second plurality of securing loops to the support casing comprises securing the lower rim to the second loop support portion, and securing the second loop support portion to the support casing.

11. The wrist brace of claim 7, the upper rims of the second plurality of loops extending outwardly from the second edge.

12. The wrist brace of claim 11, wherein the second edge comprises an edge of a removable pod unit connected to the support casing and the second loop support portion is secured to the support casing by the removable pod unit.

13. The wrist brace of claim 1, comprising a plurality of elastic securing members wherein the first and second ends of each elastic securing member are attached to the puller.

14. The wrist brace of claim 1, wherein the middle portion of the at least one elastic securing member passes through at least two of the first plurality of securing loops.

15. The wrist brace of claim 7, wherein the middle portion of the at least one elastic securing member passes through at least one of the second plurality of securing loops.

16. The wrist brace of claim 15, wherein the middle portion of each elastic securing member passes through at least two of the second plurality of securing loops.

17. The wrist brace of claim 1, wherein the support casing comprises an inner layer constructed of a material that contours to the user's wrist.

18. The wrist brace of claim 17, wherein the material is a nylon foam.

19. The wrist brace of claim 1, further comprising a strap that fits adjustably between a user's thumb and index finger.

20. A wrist brace, comprising:
   a flexible support casing including first and second longitudinal edges that are drawn together to enclose a user's wrist;
   a first plurality of securing loops, joined by a first loop support portion into a unitary structure, the first loop support portion secured to the support casing;
   at least one elastic securing member having a first end, a second end and a middle portion, wherein the middle portion passes through at least one of the first plurality of securing loops without passing through the support casing; and
   a puller, attached to the first and second ends of the at least one elastic securing member, the puller being configured to adjustably tension the at least one elastic securing member with respect to the casing.

21. The wrist brace of claim 20, wherein the first edge comprises an edge of a removable pod unit connected to the support casing and the first loop support portion is secured to the support casing by the removable pod unit.

22. The wrist brace of claim 20, further comprising a second plurality of securing loops, joined by a second loop support portion into a unitary structure, the second loop support portion secured to the support casing.

23. The wrist brace of claim 22, wherein the second edge comprises an edge of a removable pod unit connected to the support casing and the second loop support portion is secured to the support casing by the removable pod unit.

24. The wrist brace of claim 20, comprising a plurality of elastic securing members wherein the first and second ends of each elastic securing member are attached to the puller.

25. The wrist brace of claim 20, wherein the middle portion of the at least one elastic securing member passes through at least two of the first plurality of securing loops.

* * * * *